(12) United States Patent
Safarian et al.

(10) Patent No.: US 12,098,416 B2
(45) Date of Patent: Sep. 24, 2024

(54) ASSESSMENT OF BIOLOGICAL CONTAMINATION AND BIOLOGICAL CONTAMINATION TREATMENT

(71) Applicant: Halliburton Energy Services, Inc., Houston, TX (US)

(72) Inventors: Dana Safarian, Houston, TX (US); Alec Breen, Houston, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 515 days.

(21) Appl. No.: 16/833,106

(22) Filed: Mar. 27, 2020

(65) Prior Publication Data

US 2021/0017567 A1 Jan. 21, 2021

Related U.S. Application Data

(60) Provisional application No. 62/874,800, filed on Jul. 16, 2019.

(51) Int. Cl.
| | |
|---|---|
| *C12Q 1/18* | (2006.01) |
| *A01N 33/12* | (2006.01) |
| *A01N 35/02* | (2006.01) |
| *A01N 43/64* | (2006.01) |
| *A01N 57/20* | (2006.01) |
| *C09K 8/60* | (2006.01) |
| *C12Q 1/06* | (2006.01) |
| *G01N 21/78* | (2006.01) |

(52) U.S. Cl.
CPC ............. *C12Q 1/18* (2013.01); *A01N 33/12* (2013.01); *A01N 35/02* (2013.01); *A01N 43/64* (2013.01); *A01N 57/20* (2013.01); *C09K 8/605* (2013.01); *C12Q 1/06* (2013.01); *G01N 21/78* (2013.01)

(58) Field of Classification Search
CPC ... C12Q 1/18; C12Q 1/06; C12Q 1/22; A01N 33/12; A01N 35/02; A01N 43/64; A01N 57/20; A01N 43/66; C09K 8/605; G01N 21/78; G01N 21/94
See application file for complete search history.

(56) References Cited

U.S. PATENT DOCUMENTS

| | | | |
|---|---|---|---|
| 2011/0217728 A1* | 9/2011 | Yin | C12Q 1/12 435/32 |
| 2014/0303045 A1* | 10/2014 | Campbell | A01N 43/80 507/237 |
| 2017/0191108 A1* | 7/2017 | Bjork | C12Q 1/04 |
| 2018/0346955 A1* | 12/2018 | Al-Humam | C12Q 1/045 |

* cited by examiner

*Primary Examiner* — Savitha M Rao
*Assistant Examiner* — Andrew P Lee
(74) *Attorney, Agent, or Firm* — Conley Rose, P.C.; Rodney B. Carroll

(57) ABSTRACT

Systems and methods for rapidly assessing biocide contamination and biological contamination treatments found in fluids used for subterranean well treatments and related operations are provided. In some embodiments, the methods include providing a fluid including an aqueous base fluid and one or more microorganisms; introducing a first sample of the fluid to a first culture device including an indicator reagent, wherein over a period of about 48 hours or less the indicator reagent indicates a first color change in the first sample of the fluid; and determining a first count of the microorganisms in the fluid based, at least in part, on the first color change.

22 Claims, 7 Drawing Sheets

Low SRB Count (after 24H)

Bug Bottles: 0 | 1 | 2 | 3 | 4 | 5 | 6
SRB Pouches: (shading scale)

| 4H Contact | Pouches 24H | Pouches 48H | Bug Bottle 24H | Bug Bottle 48H | Bug Bottle 3 Days | Bug Bottle 8-26 Days |
|---|---|---|---|---|---|---|
| Control A |  |  | 1 | 4 | 5 | 5 |
| Control B |  |  |  |  |  |  |
| Control C |  |  |  |  |  |  |
|  |  |  |  |  |  |  |
| Glut Low A |  |  | 0 | 0 | 0 | 0 |
| Glut Low B |  |  |  |  |  |  |
| Glut Low C |  |  |  |  |  |  |
| Glut High A |  |  | 0 | 0 | 0 | 0 |
| Glut High B |  |  |  |  |  |  |
| Glut High C |  |  |  |  |  |  |
|  |  |  |  |  |  |  |
| Glut/Quat Low A |  |  | 0 | 0 | 0 | 0 |
| Glut/Quat Low B |  |  |  |  |  |  |
| Glut/Quat Low C |  |  |  |  |  |  |
| Glut/Quat High A |  |  | 0 | 0 | 0 | 0 |
| Glut/Quat High B |  |  |  |  |  |  |
| Glut/Quat High C |  |  |  |  |  |  |
|  |  |  |  |  |  |  |
| Quat Low A |  |  | 0 | 1 | 3 | 3 |
| Quat Low B |  |  |  |  |  |  |
| Quat Low C |  |  |  |  |  |  |
| Quat High A |  |  | 0 | 0 | 0 | 0 |
| Quat High B |  |  |  |  |  |  |
| Quat High C |  |  |  |  |  |  |
|  |  |  |  |  |  |  |
| THPS Low A |  |  | 1 | 3 | 5 | 5 |
| THPS Low B |  |  |  |  |  |  |
| THPS Low C |  |  |  |  |  |  |
| THPS High A |  |  | 0 | 0 | 0 | 0 |
| THPS High B |  |  |  |  |  |  |
| THPS High C |  |  |  |  |  |  |
|  |  |  |  |  |  |  |
| Preservative Low A |  |  | 0 | 1 | 3 | 6 |
| Preservative Low B |  |  |  |  |  |  |
| Preservative Low C |  |  |  |  |  |  |
| Preservative Med A |  |  | 0 | 1 | 2 | 4 |
| Preservative Med B |  |  |  |  |  |  |
| Preservative Med C |  |  |  |  |  |  |
| Preservative High A |  |  | 0 | 0 | 0 | 1 |
| Preservative High B |  |  |  |  |  |  |
| Preservative High C |  |  |  |  |  |  |

4-Hour Biocide Contact Time High TDS (1%)

FIG. 3A

| Bug Bottles | 0 | 1 | 2 | 3 | 4 | 5 | 6 |
| SRB Pouches | | | | | 4 | 5 | |

| 24H Contact | Pouches | | Bug Bottle | | | |
|---|---|---|---|---|---|---|
| | 24H | 48H | 24H | 48H | 4 Days | 7-26 Days |
| Control A | | | 6 | 12 | 12 | 12 |
| Control B | | | | | | |
| Control C | | | | | | |
| | | | | | | |
| Glut Low A | | | 0 | 0 | 0 | 2 |
| Glut Low B | | | | | | |
| Glut Low C | | | | | | |
| Glut High A | | | 0 | 0 | 0 | 0 |
| Glut High B | | | | | | |
| Glut High C | | | | | | |
| | | | | | | |
| Glut/Quat Low A | | | 0 | 0 | 0 | 0 |
| Glut/Quat Low B | | | | | | |
| Glut/Quat Low C | | | | | | |
| Glut/Quat High A | | | 0 | 0 | 0 | 0 |
| Glut/Quat High B | | | | | | |
| Glut/Quat High C | | | | | | |
| | | | | | | |
| Quat Low A | | | 4 | 6 | 6 | 6 |
| Quat Low B | | | | | | |
| Quat Low C | | | | | | |
| Quat High A | | | 3 | 5 | 5 | 6 |
| Quat High B | | | | | | |
| Quat High C | | | | | | |
| | | | | | | |
| THPS Low A | | | 5 | 5 | 6 | 6 |
| THPS Low B | | | | | | |
| THPS Low C | | | | | | |
| THPS High A | | | 0 | 0 | 0 | 0 |
| THPS High B | | | | | | |
| THPS High C | | | | | | |
| | | | | | | |
| Preservative Low A | | | 0 | 0 | 0 | 1 |
| Preservative Low B | | | | | | |
| Preservative Low C | | | | | | |
| Preservative Med A | | | 0 | 0 | 0 | 1 |
| Preservative Med B | | | | | | |
| Preservative Med C | | | | | | |
| Preservative High A | | | 0 | 0 | 0 | 0 |
| Preservative High B | | | | | | |
| Preservative High C | | | | | | |

24-Hour Biocide Contact Time High TDS (1%)

FIG.3B

Bug Bottles: 0 | 1 | 2 | 3 | 4 | 5 | 6
SRB Pouches

| 4H Contact | Pouches | | Bug Bottle | | | |
|---|---|---|---|---|---|---|
| | 24H | 48H | 24H | 48H | 3 Days | 18-26 Days |
| Control A | | | 0 | 2 | 4 | 6 |
| Control B | | | | | | |
| Control C | | | | | | |
| Glut Low A | | | 0 | 0 | 0 | 0 |
| Glut Low B | | | | | | |
| Glut Low C | | | | | | |
| Glut High A | | | 0 | 0 | 0 | 0 |
| Glut High B | | | | | | |
| Glut High C | | | | | | |
| Glut/Quat Low A | | | 0 | 0 | 0 | 0 |
| Glut/Quat Low B | | | | | | |
| Glut/Quat Low C | | | | | | |
| Glut/Quat High A | | | 0 | 0 | 0 | 0 |
| Glut/Quat High B | | | | | | |
| Glut/Quat High C | | | | | | |
| Quat Low A | | | 0 | 0 | 3 | 6 |
| Quat Low B | | | | | | |
| Quat Low C | | | | | | |
| Quat High A | | | 0 | 0 | 3 | 6 |
| Quat High B | | | | | | |
| Quat High C | | | | | | |
| THPS Low A | | | 0 | 0 | 4 | 6 |
| THPS Low B | | | | | | |
| THPS Low C | | | | | | |
| THPS High A | | | 0 | 0 | 0 | 0 |
| THPS High B | | | | | | |
| THPS High C | | | | | | |
| Preservative Low A | | | 0 | 0 | 2 | 6 |
| Preservative Low B | | | | | | |
| Preservative Low C | | | | | | |
| Preservative Med A | | | 0 | 0 | 2 | 6 |
| Preservative Med B | | | | | | |
| Preservative Med C | | | | | | |
| Preservative High A | | | 0 | 0 | 0 | 3 |
| Preservative High B | | | | | | |
| Preservative High C | | | | | | |

4-Hour Biocide Contact Time High TDS (10%)

FIG.4A

Bug Bottles: 0 | 1 | 2 | 3 | 4 | 5 | 6
SRB Pouches

| 4H Contact | Pouches | | Bug Bottle | | | |
|---|---|---|---|---|---|---|
| | 24H | 48H | 24H | 48H | 8 Days | 17-26 Days |
| Control A | | | 0 | 2 | 6 | 6 |
| Control B | | | | | | |
| Control C | | | | | | |
| | | | | | | |
| Glut Low A | | | 0 | 0 | 0 | 0 |
| Glut Low B | | | | | | |
| Glut Low C | | | | | | |
| Glut High A | | | 0 | 0 | 0 | 0 |
| Glut High B | | | | | | |
| Glut High C | | | | | | |
| | | | | | | |
| Glut/Quat Low A | | | 0 | 0 | 0 | 0 |
| Glut/Quat Low B | | | | | | |
| Glut/Quat Low C | | | | | | |
| Glut/Quat High A | | | 0 | 0 | 0 | 0 |
| Glut/Quat High B | | | | | | |
| Glut/Quat High C | | | | | | |
| | | | | | | |
| Quat Low A | | | 0 | 0 | 2 | 2 |
| Quat Low B | | | | | | |
| Quat Low C | | | | | | |
| Quat High A | | | 0 | 0 | 2 | 2 |
| Quat High B | | | | | | |
| Quat High C | | | | | | |
| | | | | | | |
| THPS Low A | | | 0 | 1 | 6 | 6 |
| THPS Low B | | | | | | |
| THPS Low C | | | | | | |
| THPS High A | | | 0 | 0 | 0 | 0 |
| THPS High B | | | | | | |
| THPS High C | | | | | | |
| | | | | | | |
| Preservative Low A | | | 0 | 0 | 6 | 6 |
| Preservative Low B | | | | | | |
| Preservative Low C | | | | | | |
| Preservative Med A | | | 0 | 0 | 3 | 3 |
| Preservative Med B | | | | | | |
| Preservative Med C | | | | | | |
| Preservative High A | | | 0 | 0 | 0 | 0 |
| Preservative High B | | | | | | |
| Preservative High C | | | | | | |

24-Hour Biocide Contact Time High TDS (10%)

FIG.4B

ASSESSMENT OF BIOLOGICAL CONTAMINATION AND BIOLOGICAL CONTAMINATION TREATMENT

CROSS-REFERENCE TO RELATED APPLICATION

The present application claims priority to U.S. Provisional Application Ser. No. 62/874,800 entitled, "Systems and Methods for Assessment of Biological Contamination and Biological Contamination Treatment" filed on Jul. 16, 2019.

BACKGROUND

The present disclosure relates to systems and methods for use in treating subterranean formations and other wellbore operations, and more specifically, systems and methods for rapidly assessing biological contamination found in fluids used for subterranean well treatments and related operations.

The presence of microorganisms, including bacteria, in fluids can lead to biological contamination of a producing formation, which is undesirable. More particularly, the presence of anaerobic bacteria (e.g., sulfate reducing bacteria (SRB)) in an oil and/or gas producing formation cause a variety of problems. If the bacteria produce sludge or slime, they can cause a reduction in the porosity of the formation which in turn reduces the production of oil and/or gas therefrom. In addition, SRB generate biofilms that stick to production tubing/pipe walls that further lead to corrosion, potential leaks, facilitation of other deposits (e.g., wax, asphaltenes, scale, etc.), and can also sour the production by producing $H_2S$ gas. For instance, the presence of hydrogen sulfide in fluids can cause excessive corrosion in metal tubular goods and surface equipment, a lower oil selling price, and the necessity to remove hydrogen sulfide from the gas prior to sale.

Microorganisms may be present in fluids used for subterranean well treatments as a result of contaminations that are present initially in the water that is used in the fluid or as a result of the recycling/reuse of fluids. The water can be contaminated with a plethora of microorganisms. Additionally, recycled fluids may be similarly contaminated as a result of having been used in the formation or stored on-site in a tank or pit.

Biocides are commonly used to counteract biological contamination. The term "biological contamination," as used herein, may refer to any living microorganism and/or by-product of a living microorganism found in fluids used in well treatments, including but not limited to SRBs, nitrate-reducing bacteria, acid-producing bacteria (APB), and the like. Because biocides are intended to kill living organisms, high doses of biocidal products pose risks to human health and welfare and the environment.

Traditional methods used to assess biological contamination and biological contamination treatment efficacy include standard "bug bottle" methods. Bug bottles may be implemented to determine the most effective biocide in reducing SRB. Depending on the conditions and properties of the fluid sample, bug bottles may require an incubation period of 28 days or more. Because such delays may be deemed too long in terms of cost, time management, or damage to the formation at a well-site in certain circumstances, contamination treatments are often preemptively administered, which may result in unnecessary costs to the operator.

BRIEF DESCRIPTION OF THE DRAWINGS

These drawings illustrate certain aspects of some of the embodiments of the present disclosure and should not be used to limit or define the claims.

FIG. 3A illustrates the results of a 4-hour biocide efficacy study in a low-TDS fluid in accordance with some embodiments of the present disclosure and a comparison of the results with a bug bottle approach.

FIG. 3B illustrates the results of a 24-hour biocide efficacy study in a low-TDS fluid in accordance with some embodiments of the present disclosure and a comparison of the results with a bug bottle approach.

FIG. 4A illustrates the results of a 4-hour biocide efficacy study in a high-TDS fluid in accordance with some embodiments of the present disclosure and a comparison of the results with a bug bottle approach.

FIG. 4B illustrates the results of a 24-hour biocide efficacy study in a high-TDS fluid in accordance with some embodiments of the present disclosure and a comparison of the results with a bug bottle approach.

Figure 1:
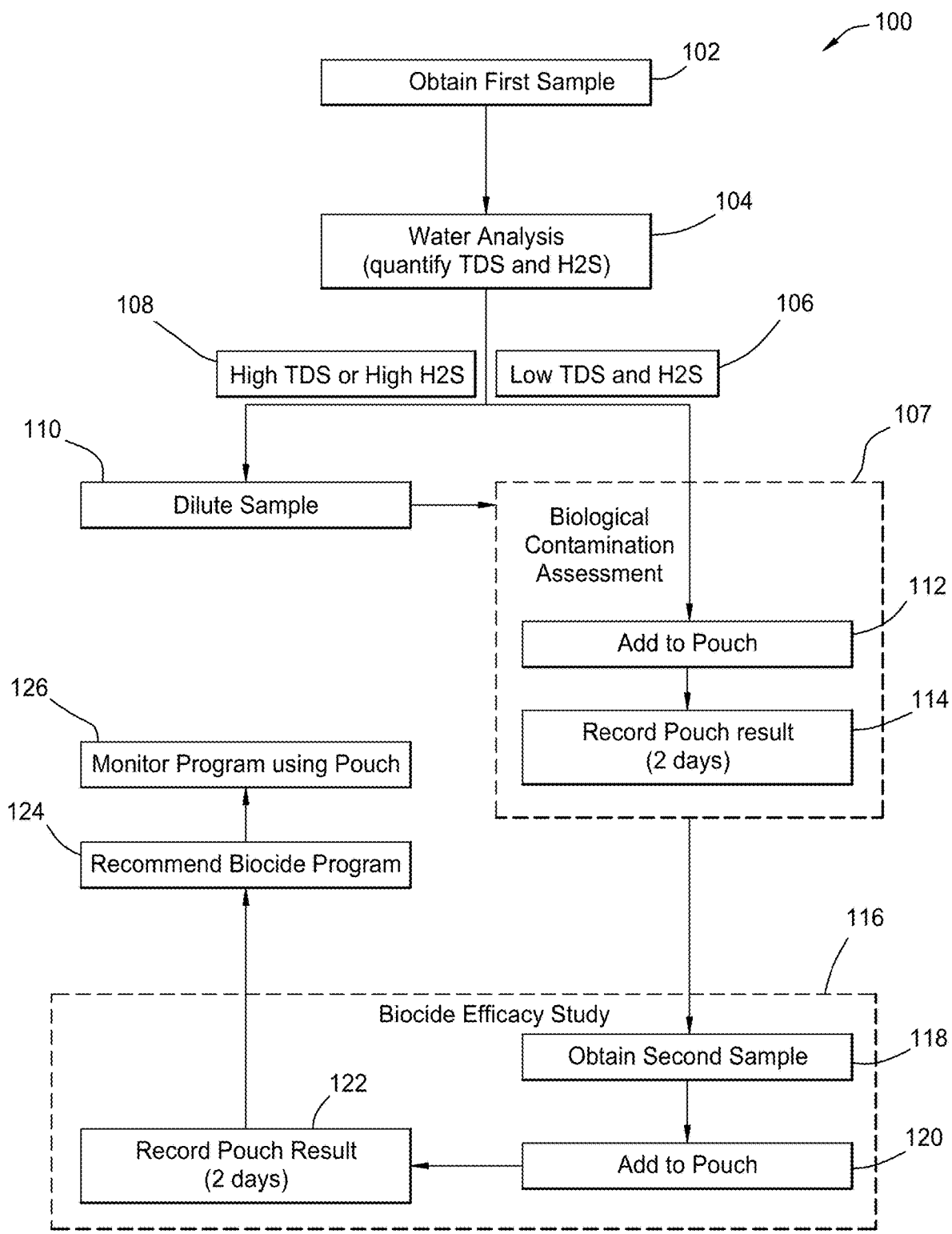
FIG. 1 is a schematic diagram illustrating a methodology for assessing biological contamination and biological contamination treatment in fluids used for oilfield operations in accordance with some embodiments of the present disclosure.

While embodiments of this disclosure have been depicted, such embodiments do not imply a limitation on the disclosure, and no such limitation should be inferred. The subject matter disclosed is capable of considerable modification, alteration, and equivalents in form and function, as will occur to those skilled in the pertinent art and having the benefit of this disclosure. The depicted and described embodiments of this disclosure are examples only, and not exhaustive of the scope of the disclosure.

DESCRIPTION OF CERTAIN EMBODIMENTS

Illustrative embodiments of the present disclosure are described in detail herein. In the interest of clarity, not all features of an actual implementation may be described in this specification. It will of course be appreciated that in the development of any such actual embodiment, numerous implementation-specific decisions may be made to achieve the specific implementation goals, which may vary from one implementation to another. Moreover, it will be appreciated that such a development effort might be complex and time-consuming but would nevertheless be a routine undertaking for those of ordinary skill in the art having the benefit of the present disclosure.

To facilitate a better understanding of the present disclosure, the following examples of certain embodiments are given. In no way should the following examples be read to limit, or define, the scope of the invention. Embodiments of the present disclosure involving wellbores may be applicable to horizontal, vertical, deviated, or otherwise nonlinear wellbores in any type of subterranean formation. Embodiments may be applicable to injection wells, monitoring wells, and production wells, including hydrocarbon or geothermal wells and retention ponds (e.g., frac ponds).

The present disclosure relates to systems and methods for use in treating subterranean formations and other wellbore operations. Particularly, the present disclosure relates to systems and methods for rapidly assessing biological contamination and treatment of biological contamination in fluids used for subterranean well treatments and related operations.

Among the many potential advantages to the systems and methods of the present disclosure, only some of which are alluded to herein, the systems and methods of the present disclosure may provide improved ability to assess biological contamination in fluids used for subterranean well treatments and related operations as compared to traditional biological contamination assessment methods. For example, in some embodiments, the systems and methods of the present disclosure may provide more accurate and faster means to design effective treatments for biological contamination in fluids. As another example, in some embodiments, the systems and methods of the present disclosure may be simpler and involve less steps than previous methods for assessing biological contamination. In some embodiments, the systems and methods of the present disclosure may provide a more accurate treatment for biological contamination and to avoid overtreatment and/or undertreatment of biological contamination. In some embodiments, the optimized biological contamination treatments provided by the systems and methods of the present disclosure may reduce the need for multiple treatments for biological contamination. In some embodiments, the optimized biological contamination treatments provided by the systems and methods of the present disclosure may reduce the quantity of biocide or other reagents used compared to traditional biological contamination tests, leading to improved economic return and production of an environmentally safe treatment fluid. In some embodiments, the systems and methods of the present disclosure may provide more rapid feedback and turnaround for assessments of biological contamination and/or the efficacy of a treatment for biological contamination compared to traditional methods. In some embodiments, the systems and methods of the present disclosure may be easier to use than traditional methods and systems. In some embodiments, the methods, compositions, and systems of the present disclosure may be simple enough to be used or performed either at a well site, in a laboratory, or at another facility at an offsite location. In some embodiments, the systems and methods of the present disclosure may reduce the space required for storage of the systems and/or performance of the methods compared to traditional methods for assessing biological contamination.

In some embodiments, the methods of the present disclosure include providing a fluid including an aqueous base fluid and one or more microorganisms; introducing a first sample of the fluid to a first culture device including an indicator reagent, wherein over a period of about 48 hours or less the indicator reagent indicates a first color change in the first sample of the fluid; and determining a first count of the microorganisms in the fluid based, at least in part, on the first color change. In some embodiments, the methods of the present disclosure include providing a fluid including an aqueous base fluid and one or more microorganisms; introducing a first sample of the fluid including a biocide to a first culture device including an indicator reagent; wherein over a period of about 48 hours or less the indicator reagent indicates a first color change in the first sample of the fluid; and determining a first count of the microorganisms in the fluid based, at least in part, on the first color change.

The fluids used in the methods and systems of the present disclosure may include any base fluid known in the art, including aqueous base fluids, non-aqueous base fluids, and any combinations thereof. The aqueous base fluids that may be suitable for use in the methods and systems of the present disclosure may include water from any source. Such aqueous fluids may include fresh water, salt water (e.g., water containing one or more salts dissolved therein), brine (e.g., saturated salt water), seawater, or any combination thereof. Suitable aqueous base fluids for the present disclosure may include virgin fluids (e.g., those that have not been used previously in a subterranean operation) and/or recycled fluids. Virgin fluids may contain water directly derived from a pond or other natural source. Recycled fluids may include those that have been used in a previous subterranean operation and/or recovered from a subterranean formation, wellbore, and or equipment used in such operations, including but not limited to drilling operations, fracturing operations, acidizing operations, cementing operations, and the like. In certain embodiments, the virgin fluids may be contaminated with a plethora of microorganisms, having an initial microorganism count in the range of about $10^3$ bacteria/mL to about to $10^9$ bacteria/mL. In some embodiments, the fluid may include $10^{10}$ bacteria/mL or greater. In certain embodiments, recycled fluids may be similarly contaminated (e.g., as a result of having been previously used in a subterranean formation or stored on-site in a contaminated tank or pit). Recycled fluids may have a microorganism count in the same range, but it may have a different bacterial contamination in that it may include different bacteria that are more resistant to treatment than those that are usually present in virgin fluids. In certain embodiments, the recycled fluids may be contaminated with a plethora of microorganisms, having an initial microorganism count in the range of about $10^3$ bacteria/mL to about to $10^9$ bacteria/mL. In some embodiments, the fluid may include $10^{10}$ bacteria/mL or greater.

In some embodiments, a sample of the fluid is introduced into one or more culture devices (e.g., thin-film culture devices). In some embodiments, the culture device may include a body including a waterproof base, waterproof coversheet, and a growth compartment disposed between the base and the coversheet. The growth compartment may have a perimeter that includes an opening. The opening provides liquid access to the growth compartment. In certain embodiments, the base may include a relatively stiff waterproof film made of a material that will not absorb or otherwise be adversely affected by water. Examples of materials suitable for the base in certain embodiments of the present disclosure include, but are not limited to polyester, polypropylene, polystyrene, ethylene vinyl alcohol copolymer films, polyvinyl alcohol films, polyvinylidene chloride films, and the like. The base may include a material that is substantially non-transmissible to gaseous oxygen. In some embodiments, the base may be opaque, translucent, or, transparent (e.g., if observing colonies through the base is desired). The coversheet may be attached (e.g., adhesively attached) to the base to define the growth compartment. In some embodiments, the coversheet may be optically transmissive (e.g. to view the growth compartment during shipping, storage, incubation, and/or colony counting). The coversheet may include a relatively stiff waterproof film made of a material that will not absorb or otherwise be adversely affected by water. Examples of materials suitable for the base in certain embodiments of the present disclosure include, but are not limited to polyester, polypropylene, polystyrene, ethylene vinyl alcohol copolymer films, polyvinyl alcohol films, and polyvinylidene chloride films, and the like. In certain embodiments, the coversheet may be transparent in order to facilitate the counting of microorganism colonies without opening the culture device and may be substantially impermeable to microorganisms and water vapor. In certain embodiments, the coversheet may be made of the same or different material as the base. In some embodiments, the coversheet may be made using a material that is substantially non-transmissible to gaseous oxygen. A person having ordinary skill in the art will recognize the transmissibility of oxygen gas through a given type of polymer film may be reduced by increasing the thickness of the polymer film. In some embodiments, the base and coversheet of the present disclosure are polymeric films having a suitable thickness to be substantially non-transmissible to gaseous oxygen.

In some embodiments, the culture device of the present disclosure may include an indicator reagent, a nutrient or nutrient culture medium, and a gelling agent disposed in the growth compartment. In some embodiments, these chemical components do not require salinity matching and are compatible with any level of total dissolved solids (TDS) contained in any one fluid sample. In some embodiments, the sample of fluid introduced into the culture device does not require dilution and/or serial dilution. In some embodiments, the sample of fluid introduced into the culture device may be diluted and/or serially diluted.

In some embodiments, the indicator reagent disposed in the growth compartment may detect biological contamination. In some embodiments, the indicator reagent may be disposed in the growth compartment as a loose powder or distributed onto the inner surface of the base and/or the inner surface of the coversheet in the growth compartment of the culture device.

In certain embodiments, the indicator reagent may detect microorganisms and/or byproducts thereof. In certain embodiments, the indicator reagent may detect anaerobic bacteria such as sulfate-reducing bacteria (SRB), nitrate-reducing bacteria, acid producing bacteria (APB), and the like, and/or byproducts thereof. In some embodiments, detecting the SRB may include detecting SRB (e.g., visually or using machine vision) in a sample of fluid introduced into a culture device. In some embodiments, detecting the SRB in the culture device may include detecting a change in the sample of fluid associated with the indicator reagent and/or caused by the indicator reagent. For example, the indicator reagent may react with SRB and/or byproducts thereof included in the sample of fluid in a detectable manner (e.g., visually or using machine vision). Examples of materials suitable for the indicator reagent in certain embodiments of the present disclosure include but are not limited to reagents for detecting hydrogen sulfide production by microorganisms, a pH indicator, a redox indicator, a chromogenic enzyme substrate, a fluorogenic enzyme substrate, any combination thereof, and the like. In some embodiments, suitable indicator reagents may include, but are not limited to, one or more iron-containing compounds such as one or more ferrous salts. Examples of indicator reagents suitable for certain embodiments of the present disclosure include, but are not limited to, ferric ammonium citrate, ferrous sulfate, ammonium ferric sulfate, any derivative thereof, and any combination thereof.

In some embodiments, the indicator reagent may change and/or cause a change of a sample of fluid from a first state (e.g., substantially colorless or nonfluorescent) to a second state (e.g., colored or fluorescent) when the sample of fluid includes any microorganisms or a detectable quantity of microorganisms (e.g., bacteria/mL). In some embodiments, the change in state may be directly related to the count of microorganisms in the sample of fluid. For example, in certain embodiments, an iron-based indicator reagent may be introduced into a sample of fluid including SRB and react with hydrogen sulfide produced by the SRB to form a visually detectable and quantifiable amount of iron precipitate. In some embodiments, the degree and/or rate of a color change associated with the amount of iron precipitate produced may be directly related to the count of bacteria (e.g., bacteria/mL). For example, the degree of blackening of the sample of fluid due to the formation of iron sulfides may be indicative of the SRB count.

In certain embodiments, the methods of the present disclosure detect biological contamination over a period of about 50 hours or less. In certain embodiments, the methods of the present disclosure detect biological contamination over a period of about 36 hours or less. In certain embodiments, the methods of the present disclosure detect biological contamination over a period of about 24 hours or less. In certain embodiments, the methods of the present disclosure detect biological contamination over a period of about 12 hours or less. In certain embodiments, the methods of the present disclosure detect biological contamination over a period of about 40, about 35, about 30, about 25, about 20, or about 15 hours or less. In certain embodiments the methods of the present disclosure detect biological contamination over a period of about 24 to about 48 hours or less. In certain embodiments, the methods of the present disclosure detect biological contamination over a period of about 24 to about 50 hours or less. In certain embodiments, the methods of the present disclosure detect biological contamination over a period of about 24 to about 32 hours or less.

In some embodiments, the methods of the present disclosure may determine a count of the microorganisms in a sample of fluid, based, at least in part, on a color change over a period of time. In some embodiments, the degree of color change over a period of about 24 hours or less may correspond to a microorganism count in the range of about $10^3$ bacteria/mL to about to $10^9$ bacteria/mL. In some embodiments, the degree of color change over a period of about 48 hours or less may correspond to a microorganism count in the range of about $10^3$ bacteria/mL to about to $10^9$ bacteria/mL. In some embodiments, the degree of color change over a period of about 24-32 hours may correspond to a microorganism count in the range of about $<10^4$ bacteria/mL. In some embodiments, the degree of color change over a period of about 24-32 hours may correspond to a microorganism count in the range of about $10^4$ bacteria/mL. In some embodiments, the degree of color change over a period of about 24-32 hours may correspond to a microorganism count in the range of about $\geq 10^5$ bacteria/mL. In some embodiments, the degree of color change over a period of about 42-50 hours may correspond to a microorganism count in the range of about $\leq 10^1$ bacteria/mL. In some embodiments, the degree of color change over a period of about 42-50 hours may correspond to a microorganism count in the range of about $10^2$ bacteria/mL. In some embodiments, the degree of color change over a period of about 42-50 hours may correspond to a microorganism count in the range of about $\geq 10^3$ bacteria/mL.

In some embodiments, a nutrient or nutrient culture medium may be disposed in the growth compartment of the culture device. In some embodiments, the nutrient or nutrient culture medium may be cold-water-reconstitutable. In some embodiments, the nutrient or nutrient culture medium may facilitate growth of SRB. In some embodiments, the nutrient or culture medium in the culture device may depend on the microorganism to be grown in the culture device. A person of skill in the art, with the benefit of this disclosure, will understand which nutrient or culture mediums are suitable for detecting microorganisms in the culture device. Examples of nutrient culture medium suitable for certain embodiments of the present disclosure include, but are not limited to Bacto Tryptone, Amresco Soytone, Bacto Yeast Extract, $MgSO_4$-$7H_2O$, sodium lactate, sodium acetate, NaCl, $NH_4Cl$, and any combination thereof. Examples of nutrients for supporting bacterial growth suitable for certain embodiments of the present disclosure include, but are not limited to yeast extract, peptone, sugars, suitable salts, and the like, and any combination thereof. In some embodiments, a selective agent (e.g., a nutrient, an antibiotic, and combinations thereof) that facilitates the growth of SRB or group of SRB over another microorganism or group of microorganisms that may otherwise grow in the culture device may be disposed in the growth compartment of the culture device. Those skilled in the art will recognize that a variety of other formulations that could be used and that these do not detract from the scope of this disclosure. Those skilled in the art will additionally recognize that the culture devices can be similarly designed facilitate the growth of and detect other microorganisms such as nitrate-reducing bacteria, acid producing bacteria (APB), and the like.

In some embodiments, the gelling agent may be cold-water-soluble. In some embodiments, the gelling agent may be adhered, either directly or indirectly, to the base and/or the coversheet. In some embodiments, the gelling agent may be uniformly distributed onto the inner surface of the base and/or the inner surface of the coversheet in the growth compartment of the culture device. Examples of gelling agents suitable for certain embodiments of the present disclosure include, but are not limited to algin, carboxymethyl cellulose, tara gum, hydroxyethyl cellulose, guar gum, locust bean gum, xanthan gum, a synthetic gelling agent, and any derivatives or combinations thereof. In some embodiments, synthetic gelling agents suitable for certain embodiments of the present disclosure include, but are not limited to include, but are not limited to polyacrylamide, polyurethane, polyethylene oxides, hydroxypropyl methylcellulose.

In some embodiments, the methods and culture devices of the present disclosure may be used to determine whether to treat the biological contamination of a fluid. In some embodiments, the methods and culture devices of the present disclosure may be used to determine whether to treat the biological contamination based on the microorganism count of a sample of fluid in the culture device. In some embodiments, the culture device may be used to determine whether to treat the biological contamination based on the microorganism count determined after a period of about 48 hours or less, where a higher count of microorganisms translates to a higher likelihood of treatment and/or higher treatment dosage.

In some embodiments, a contamination treatment such as a biocide and/or UV light treatment may be introduced to the sample fluid contained in a culture device. For wellbore use, commonly used biocides are any of the various commercially available biocides that kill microorganisms upon contact, and which are compatible with the treatment fluids utilized and the components of the formation. For example, biocides suitable for certain embodiments of the present disclosure may include, but are not limited to, quaternary ammonium compounds, chlorine, hypochlorite solutions, sodium dichloro-s-triazinetrione, glutaraldehyde, quaternary phosphonium compounds, isothiazolinones, oxazolidine, sodium bromide, chlorine dioxide, bronopol, triazine, chlorine dioxide, peracetic acid, 2,2-dibromo-3-nitrilopropionamide (DBNPA), acrolein, and the like, and any combination thereof. In some embodiments, the appropriate dose of the biocide introduced into the sample fluid may be determined based on the Environmental Protection Agency (EPA) dosage regulations for each particular biocide. In some embodiments, the appropriate dose of the biocide introduced into the sample fluid may be determined based on the suggested dosages on the packaging for each particular biocide. In some embodiments, a contamination treatment may include exposing the fluid to UV light. Examples of germicidal wavelengths suitable for certain embodiments of the present disclosure include but are not limited to high intensity UV light such as UV-C light.

In certain embodiments, the sample fluid used in the methods and systems of the present disclosure optionally may include any number of additional additives. Examples of such additional additives include, but are not limited to, salts, surfactants, acids, proppant particulates, diverting agents, fluid loss control additives, gas, nitrogen, carbon dioxide, surface modifying agents, tackifying agents, foamers, corrosion inhibitors, scale inhibitors, catalysts, clay control agents, biocides, friction reducers, antifoam agents, bridging agents, flocculants, additional $H_2S$ scavengers, $CO_2$ scavengers, oxygen scavengers, lubricants, additional viscosifiers, breakers, weighting agents, relative permeability modifiers, resins, wetting agents, coating enhancement agents, filter cake removal agents, antifreeze agents (e.g., ethylene glycol), and the like. In certain embodiments, one or more of these additional additives may be added to the sample fluid and/or activated before and/or after the biocide has been introduced. A person skilled in the art, with the benefit of this disclosure, will recognize the types of additives that may be included in the fluids of the present disclosure for a particular application.

In some embodiments, one or more culture devices may be used to determine the effectiveness of a biocide and/or other contamination treatments. In some embodiments, the culture devices may be used to compare various biocides and/or other contamination treatments in one or more biocide efficacy studies. In certain embodiments, the culture devices may be used to optimize a contamination treatment. In some embodiments, a sample of fluid containing a biocide is introduced in the culture device to obtain a count of microorganisms in the treated fluid sample. In some embodiments, the count of microorganisms in the treated fluid sample is compared to a count of microorganisms in an untreated sample of the fluid in order to determine the effectiveness of the biocide and to determine a biocide program. In some embodiments, a count of microorganisms in a first fluid sample treated with a first biocide is compared to a count of microorganisms in second fluid sample treated with a second biocide in order to determine the effectiveness of a biocide and to determine a biocide program.

In some embodiments, the methods and systems of the present disclosure may be used to determine which biocide or combination thereof will be used to treat a fluid based, at least in part, on the microorganism count of a sample of the fluid treated with the biocide(s). In some embodiments, the culture device may be used to determine biocide efficacy within a period of about 48 hours or less after biocide treatment.

In some embodiments, the culture devices may be used to monitor the progress of biocide treatments and/or other contamination treatments. In some embodiments, a fluid samples from a treated fluid are retrieved and introduced to new culture devices to monitor the continued efficacy of the biocide and/or to determine whether the microorganisms have become resistant to the current treatment. In some embodiments, for example where the SRB have become resistant to the biocide, a new efficacy study may be performed using the culture devices to modify the biocide treatment and/or other contamination treatment.

FIG. 1 is a schematic diagram illustrating a methodology for assessing biological contamination and biological contamination treatment in fluids used for oilfield operations in accordance with some embodiments of the present disclosure 100. In some embodiments, a fluid including an aqueous base fluid and an unknown microorganism count is provided. In some embodiments, a first sample of the fluid is obtained 102. In certain embodiments, the first sample of the fluid may have a volume in the range about 0.5 mL to about 10 mL. In certain embodiments, the first sample of the fluid may have a volume in the range about 1 mL to about 5 mL. In certain embodiments, the first sample of the fluid may have a volume of about 4 mL or less. In certain embodiments, the first sample of the fluid may have a volume of about 3 mL or less. In certain embodiments, the first sample of the fluid may have a volume of about 2 mL or less. In certain embodiments, the first sample of the fluid may have a volume of about 1 mL or less.

In some embodiments, the first sample may be analyzed for total dissolved solids (TDS) and $H_2S$ concentration 104. In some embodiments, a biological contamination assessment may be performed 107. In certain embodiments, a first sample with a low TDS and low $H_2S$ concentration 106 may be introduced to the growth compartment of a culture device (e.g., a "pouch") including an indicator reagent 112. In certain embodiments, a first sample with a high TDS and/or high $H_2S$ concentration 108 may be diluted to a TDS of about 20% or less and/or $H_2S$ concentration of about 25 parts per million (ppm) of less before being added to the culture device 112.

In some embodiments, a biological contamination assessment may be performed. In some embodiments, the rate and degree of color change of the indicator reagent of the culture device may be recorded. In some embodiments, the rate and degree of color change by the indicator reagent of the culture device may be recorded after a period of about 48 hours or less 114. In some embodiments, the rate and degree of color change may be corresponded to a first microorganism count of the first sample of the fluid. In some embodiments, the rate and degree of color change may be corresponded to a first microorganism count of the first sample of the fluid based on predetermined data. In some embodiments, the rate and degree of color change may be corresponded to a first microorganism count of the first sample of the fluid based on a known correlation. For example, in some embodiments, the degree of color change over a period of about 24 hours or less may correspond to a reference color that indicates a first microorganism count in the range of about $10^3$ bacteria/mL to about to $10^9$ bacteria/mL. For example, in some embodiments, the degree of color change over a period of about 48 hours or less may correspond to a reference color reference color that indicates a first microorganism count in the range of about $10^3$ bacteria/mL to about to $10^9$ bacteria/mL. For example, in some embodiments, the degree of color change over a period of about 24-32 hours may correspond to a reference color that indicates a first microorganism count in the range of about $<10^4$ bacteria/mL. For example, in some embodiments, the degree of color change over a period of about 24-32 hours may correspond to a reference color that indicates a first microorganism count in the range of about $10^4$ bacteria/mL. For example, in some embodiments, the degree of color change over a period of about 24-32 hours may correspond to a reference color that indicates a first microorganism count in the range of about $\geq 10^5$ bacteria/mL. For example, in some embodiments, the degree of color change over a period of about 42-50 hours may correspond to a reference color that indicates a first microorganism count in the range of about $\leq 10^1$ bacteria/mL. For example, in some embodiments, the degree of color change over a period of about 42-50 hours may correspond to a reference color that indicates a first microorganism count in the range of about $10^2$ bacteria/mL. For example, in some embodiments, the degree of color change over a period of about 42-50 hours may correspond to a reference color that indicates a first microorganism count in the range of about $\geq 10^3$ bacteria/mL.

One of ordinary skill in the art with the benefit of this disclosure would understand that multiple culture device experiments assessing biological contamination in multiple samples from the same or different sources and/or different dilutions of the same samples may be run concurrently.

In some embodiments, a biocide efficacy study may be performed 116. In some embodiments, the biocide efficacy study may be performed after the biological contamination assessment has been performed 107. In some embodiments, a second sample of the fluid may be obtained 118 and introduced to the growth compartment of a second culture device 120. In some embodiments, the rate and degree of color change of the indicator reagent of the second culture device may be recorded. In some embodiments, the rate and degree of color change by the indicator reagent of the second culture device may be recorded after a period of about 48 hours or less 122. In some embodiments, the rate and degree of color change may be corresponded to a second microorganism count of the second sample of the fluid. In some embodiments, the rate and degree of color change may be corresponded to a second microorganism count of the second sample of the fluid based on predetermined data. In some embodiments, the rate and degree of color change may be corresponded to a second microorganism count of the second sample of the fluid based on a known correlation. For example, in some embodiments, the degree of color change over a period of about 24 hours or less may correspond to a reference color that indicates a second microorganism count in the range of about $10^3$ bacteria/mL to about to $10^9$ bacteria/mL. For example, in some embodiments, the degree of color change over a period of about 48 hours or less may correspond to a reference color reference color that indicates a second microorganism count in the range of about $10^3$ bacteria/mL to about to $10^9$ bacteria/mL. For example, in some embodiments, the degree of color change over a period of about 24-32 hours may correspond to a reference color that indicates a second microorganism count in the range of about $<10^4$ bacteria/mL. For example, in some embodiments, the degree of color change over a period of about 24-32 hours may correspond to a reference color that indicates a second microorganism count in the range of about $10^4$ bacteria/mL. For example, in some embodiments, the degree of color change over a period of about 24-32 hours may correspond to a reference color that indicates a second microorganism count in the range of about $\geq 10^5$ bacteria/mL. For example, in some embodiments, the degree of color change over a period of about 42-50 hours may correspond to a reference color that indicates a second microorganism count in the range of about $\leq 10^1$ bacteria/mL. For example, in some embodiments, the degree of color change over a period of about 42-50 hours may correspond to a reference color that indicates a second microorganism count in the range of about $10^2$ bacteria/mL. For example, in some embodiments, the degree of color change over a period of about 42-50 hours may correspond to a reference color that indicates a second microorganism count in the range of about ≥$10^3$ bacteria/mL.

In some embodiments, a biocide program is recommended based on the results of the biocide efficacy study 124. In some embodiments, if the results of a biocide efficacy study demonstrate a second microorganism count that is acceptably lower than the first microorganism count, a biocide program using the biocide from the biocide efficacy study may be used for treating the fluid. If the results of the biocide efficacy study demonstrate a second microorganism count that is insignificantly lower or higher than the first microorganism count, a biocide program using the biocide from the biocide efficacy study may not be used for treating the fluid. One of ordinary skill in the art will appreciate that multiple culture device experiments may be run at the same time using different combinations of biocides and/or different doses of the same biocide. In some embodiments, the different biocides and/or different dosages may be compared in order to select an optimal biocide and/or dosage thereof for the fluid. In some embodiments, the biocide program may include contacting the fluid with the selected biocide to produce a treatment fluid for use in various oilfield operations.

In some embodiments, the biocide program for the fluid may be monitored 126. In some embodiments, the biocide program may be monitored by performing additional biological contamination assessments 107 and biocide efficacy studies 116 on one or more additional samples of the fluid as at least one or more portions of the fluid are used for various oilfield operations. For example, in some embodiments, additional biological contamination assessments 107 and biocide efficacy studies 116 may be performed any time before at least a portion of a biocide-treated fluid is introduced into a wellbore penetrating at least a portion of a subterranean formation.

To facilitate a better understanding of the present disclosure, the following examples of certain aspects of certain embodiments are given. The following examples are not the only examples that could be given according to the present disclosure and are not intended to limit the scope of the disclosure or claims.

EXAMPLES

Example 1

Figure 2A:
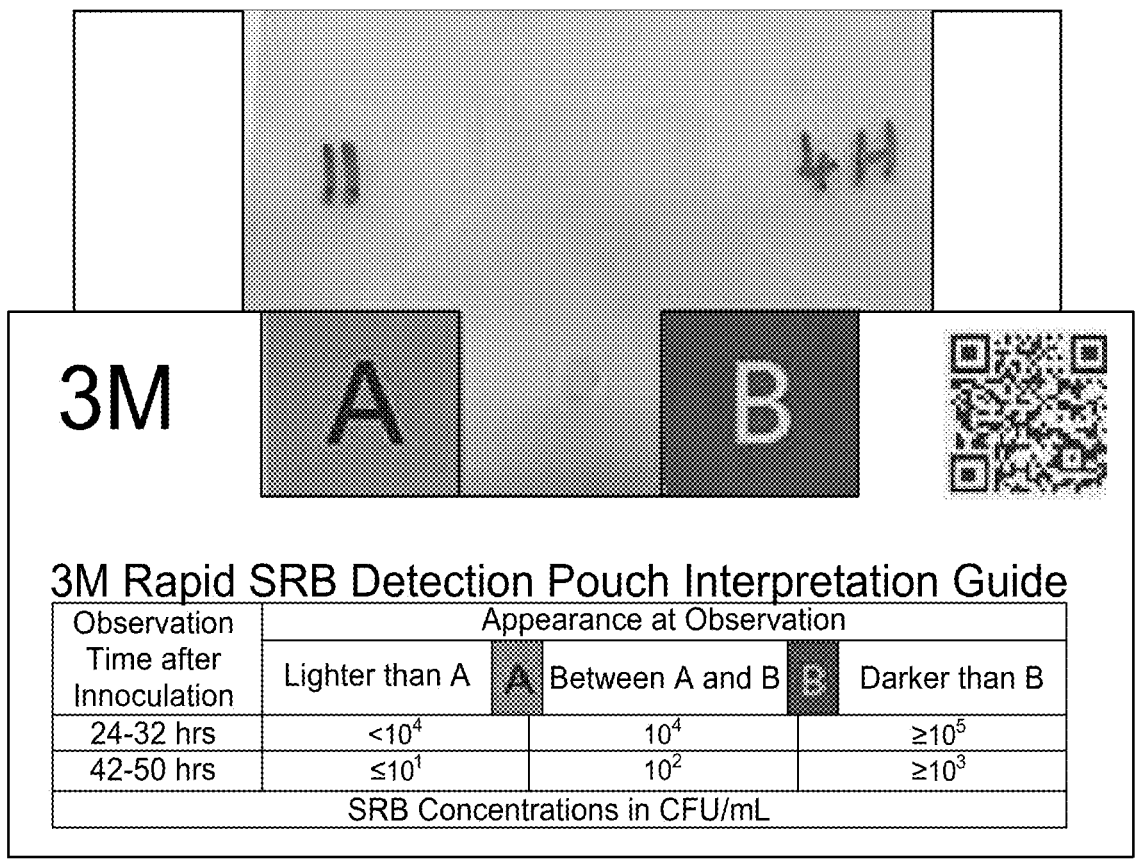
FIG. 2A is a photograph illustrating the results of an SRB detection pouch test for a fluid having a low SRB count in accordance with some embodiments of the present disclosure.
Figure 2B:
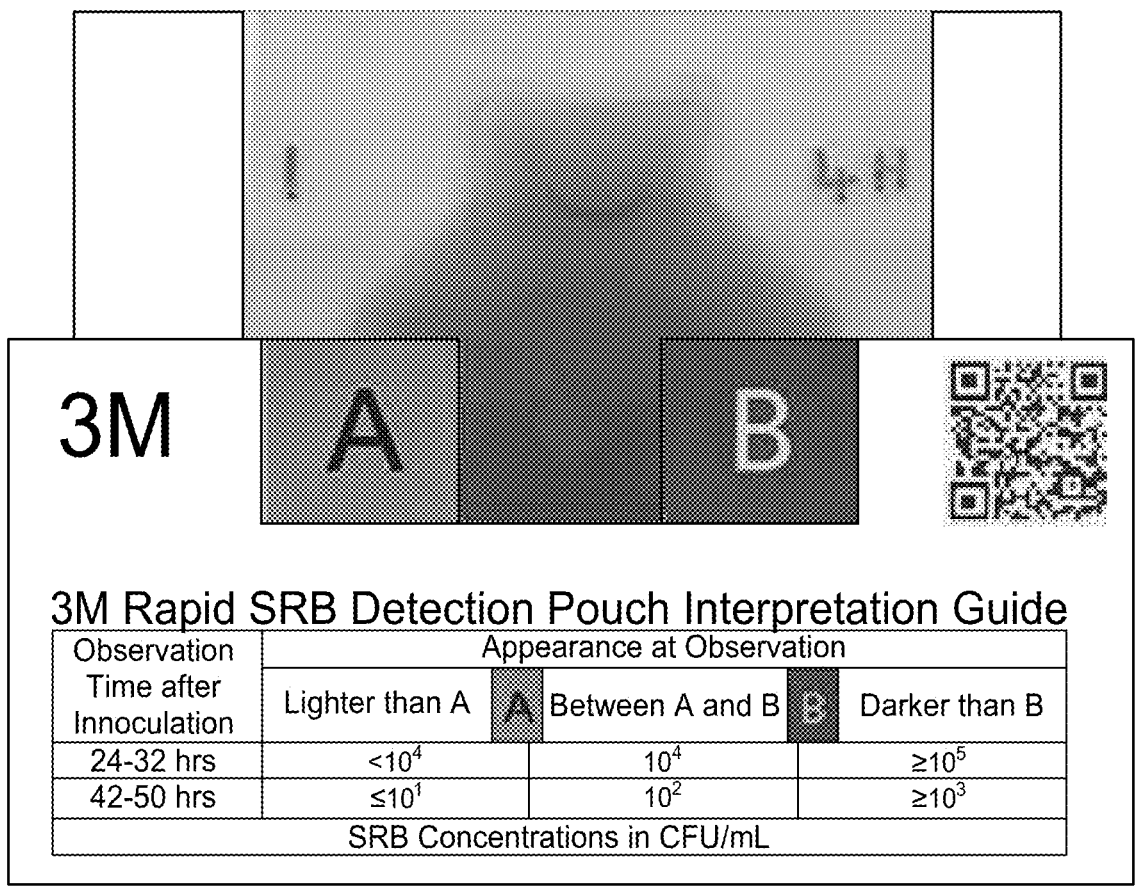
FIG. 2B is a photograph illustrating the results of an SRB detection pouch test for a fluid having a high SRB count in accordance with some embodiments of the present disclosure.

In this example, an assessment of biological contamination was performed using culture devices including indicator reagents. More specifically, SRB enumeration in various water samples including SRB was performed using thin-film culture devices ("pouches"). Three milliliters of two samples, Sample A and Sample B, were introduced into separate Rapid SRB Detection Pouches (manufactured by 3M™). The pouches were sealed and incubated at 32° C. The pouches were incubated upright to allow the precipitate to settle toward the bottom of pouch. The SRB count of each sample was measured at multiple time intervals using a visual technique where the color of the samples was compared to reference colors as shown in FIGS. 2A and 2B. The degree of blackening of the sample at certain time points compared to the reference is indicative of SRB count.

At approximately 24 hours of incubation, the SRB count of Sample A was confirmed at <$10^4$ bacteria per milliliter (bacteria/mL). After approximately 42 hours, another measurement was taken and the SRB count of Sample A was confirmed at ≤$10^1$ bacteria/mL. After 24 hours, the SRB count of Sample B was confirmed as ≥$10^4$ bacteria/mL. Traditional dilution vials were used to confirm that Sample A contained less than $10^4$ bacteria/mL SRB and Sample B contained $10^6$ bacteria/mL SRB. These data demonstrate that the thin-film culture devices effectively deliver rapid and accurate SRB detection.

Example 2

A biocide efficacy study on a low TDS (1%) fluid sample using a thin-film culture device was evaluated and compared to the traditional bug-bottle approach. The low TDS fluid sample was inoculated with mature SRB. Seventy-two 3 mL doses of the fluid sample were then introduced into 72 Rapid SRB Detection Pouches. Six of the pouches were reserved as control groups while half of the remaining pouches were treated for approximately 4-hour biocide contact and the other half for approximately 24-hour biocide contact times at low, medium, and high dosages of the following biocides: glutaraldehyde (Glut), tetrakis(hydroxymethyl)phosphonium sulfate (THPS), didecyldimethyl ammonium chloride (Quat), glutaraldehyde/benzalkonium chloride blend (Glut/Quat), and triazine (Preservative). The dosages were based on the standard US Environmental Protection Agency (EPA) recommendations for each respective biocide:

| Biocide | Dose |
|---|---|
| Glut Low | 100 ppm |
| Glut High | 500 ppm |
| Glut/Quat Low | 118 ppm |
| Glut/Quat High | 500 ppm |
| Quat Low | 20 ppm |
| Quat High | 100 ppm |
| THPS Low | 25 ppm |
| THPS High | 500 ppm |
| Preservative Low | 100 ppm |
| Preservative Med | 150 ppm |
| Preservative High | 250 ppm |

The fluid samples were then incubated at a temperature of 32° C. After approximately 24 hours of inoculation, the SRB count was measured using the incubation and referencing procedure of Example 1. The bug bottle numbers were determined by counting the number of bottles in a serial dilution which had formed a visible black precipitate. Those measurements are shown in FIGS. 3A and 3B. The SRB count of the control group pouches for both the 4-hour contact group and the 24-hour contact group after approximately 24 hours was $10^4$ bacteria/mL and after approximately 48 hours was ≥$10^3$ bacteria/mL. For the 4-hour biocide contact time group, all but the THPS Low biocide group demonstrated a reduction in SRB count in comparison to the control. The glutaraldehyde high dose, glutaraldehyde/benzalkonium chloride blend high dose, THPS high dose, and triazine high dose biocide groups demonstrated the highest effectiveness with an SRB count of ≤$10^1$ bacteria/mL after approximately 48 hours. For the 24-hour biocide contact time group, all but the didecyldimethyl ammonium chloride and THPS low dose biocide groups demonstrated a reduction in SRB count. The glutaraldehyde high dose, glutaraldehyde/benzalkonium chloride blend, THPS high dose, and triazine biocide groups were the most effective, with an SRB count of ≤$10^1$ bacteria/mL after approximately 48 hours. As shown in FIGS. 3A and 3B, the bug bottle method only delivered accurate SRB counts after 3 or more days. These data demonstrate that the thin-film culture devices effectively deliver rapid and accurate biocide efficacy studies at a low TDS (1%).

Example 3

A biocide efficacy study on a high TDS (10%) fluid sample using a thin-film culture device was evaluated and compared to the traditional bug-bottle approach. The high TDS fluid sample was inoculated with mature SRB. Seventy-two 3 mL doses of the fluid sample were then introduced into 72 respective Rapid SRB Detection Pouches. Six of the pouches were reserved as control groups while half of the remaining pouches were treated for an approximately 4-hour biocide contact time and the other half for a 24-hour biocide contact time at low, medium, and high dosages of the following biocides: glutaraldehyde (Glut), tetrakis(hydroxymethyl)phosphonium sulfate (THPS), didecyldimethyl ammonium chloride (Quat), glutaraldehyde/benzalkonium chloride blend (Glut/Quat), and triazine (Preservative). The dosages were based on the standard US Environmental Protection Agency (EPA) recommendations for each respective biocide:

| Biocide | Dose |
|---|---|
| Glut Low | 100 ppm |
| Glut High | 500 ppm |
| Glut/Quat Low | 118 ppm |
| Glut/Quat High | 500 ppm |
| Quat Low | 20 ppm |
| Quat High | 100 ppm |
| THPS Low | 25 ppm |
| THPS High | 500 ppm |
| Preservative Low | 100 ppm |
| Preservative Med | 150 ppm |
| Preservative High | 250 ppm |

The fluid samples were then incubated at a temperature of 32° C. After approximately 24 hours of inoculation, the SRB count was measured using the incubation and referencing procedure of Example 1. The bug bottle numbers were determined by counting the number of bottles in a serial dilution which had formed a visible black precipitate. Those measurements are shown in FIGS. 4A and 4B. The SRB count of the control group pouches for both the 4-hour contact group and the 24-hour contact group after approximately 24 hours was $10^4$ bacteria/mL and after approximately 48 hours was $\geq 10^3$ bacteria/mL. For the 4-hour biocide contact time group, all but the Quat and THPS low dose biocide groups demonstrated a reduction in SRB count in comparison to the control. The glutaraldehyde, glutaraldehyde/benzalkonium chloride blend, and THPS high dose biocide groups demonstrated the highest effectiveness with an SRB count of $\leq 10^1$ bacteria/mL after approximately 48 hours. For the 24-hour biocide contact time group, all biocide groups demonstrated a reduction in SRB count. The glutaraldehyde, glutaraldehyde/benzalkonium chloride blend, THPS high dose, and triazine high dose biocide groups were the most effective, with an SRB count of $\leq 10^1$ bacteria/mL after approximately 48 hours. As shown in FIGS. 4A and 4B, the bug bottle method only delivered accurate SRB counts after 3 or more days. These data demonstrate that the thin-film culture devices effectively deliver rapid and accurate biocide efficacy studies at a high TDS (10%).

An embodiment of the present disclosure is a method including providing a fluid including an aqueous base fluid and one or more microorganisms; introducing a first sample of the fluid to a first culture device including an indicator reagent, wherein over a period of about 48 hours or less the indicator reagent indicates a first color change in the first sample of the fluid; and determining a first count of the microorganisms in the fluid based, at least in part, on the first color change. In some embodiments, the fluid is a recycled fluid. In some embodiments, the indicator reagent is selected from the group consisting of ferric ammonium citrate, ferrous sulfate, ammonium ferric sulfate, any derivative thereof, and any combination thereof. In some embodiments, at least one of the one or more microorganisms includes sulfate reducing bacteria (SRB). In some embodiments, the first sample of the fluid has less than 1% total dissolved solids by weight. In some embodiments, the first sample of the fluid has greater than 10% total dissolved solids by weight. In some embodiments, the method further includes determining a biocide for treating the fluid based, at least in part, on the first count of the microorganisms in the fluid. In some embodiments, the method further includes introducing the biocide into the fluid to produce a treatment fluid; and introducing the fluid into a wellbore penetrating at least a portion of a subterranean formation.

Another embodiment of the present disclosure is a method including providing a fluid including an aqueous base fluid and one or more microorganisms; introducing a first sample of the fluid including a biocide to a first culture device including an indicator reagent; wherein over a period of about 48 hours or less the indicator reagent indicates a first color change in the first sample of the fluid; and determining a first count of the microorganisms in the fluid based, at least in part, on the first color change. In some embodiments, the biocide is selected from the group consisting of a quaternary ammonium compound, chlorine, a hypochlorite solution, sodium dichloro-s-triazinetrione, glutaraldehyde, a quaternary phosphonium compound, an isothiazolinone, oxazolidine, sodium bromide, chlorine dioxide, bronopol, triazine, chlorine dioxide, peracetic acid, 2,2-dibromo-3-nitrilopropionamide (DBNPA), acrolein, and any combination thereof. In some embodiments, the fluid is a recycled fluid. In some embodiments, the indicator reagent is selected from the group consisting of ferric ammonium citrate, ferrous sulfate, ammonium ferric sulfate, any derivative thereof, and any combination thereof. In some embodiments, at least one of the one or more microorganisms includes sulfate reducing bacteria (SRB). In some embodiments, the first sample of the fluid has less than 1% total dissolved solids by weight. In some embodiments, the first sample of the fluid has greater than 10% total dissolved solids by weight. In some embodiments, the method further includes determining a biocide for treating the fluid based, at least in part, on the first count of the microorganisms in the fluid. In some embodiments, the method further includes introducing the biocide into the fluid to produce a treatment fluid; and introducing the fluid into a wellbore penetrating at least a portion of a subterranean formation.

Another embodiment of the present disclosure is a method including providing a fluid including an aqueous base fluid and one or more microorganisms; introducing a first sample of the fluid including a first biocide to a first culture device including a first indicator reagent, wherein over a period of about 48 hours or less the first indicator reagent indicates a first color change in the first sample of the fluid; determining a first count of the microorganisms in the first sample of the fluid based, at least in part, on the first color change; introducing a second sample of the fluid including a second biocide to a second culture device including a second indicator reagent, wherein over a period of about 48 hours or less the second indicator reagent indicates a second color change in the second sample of the fluid; determining a second count of the microorganisms in the second sample of the fluid based, at least in part, on the second color change; selecting a treatment biocide from the first biocide and the second biocide, based, at least in part, on a comparison of the first count of the microorganisms and the second count of the microorganisms; contacting the fluid with the treatment biocide to produce a treatment fluid; and introducing the treatment fluid into a wellbore penetrating at least a portion of a subterranean formation. In some embodiments, the method further includes contacting the fluid with the treatment biocide for at least a period of about four hours before introducing the treatment fluid into the wellbore. In some embodiments, the method further includes contacting the fluid with the treatment biocide for at least a period of about twenty-four hours before introducing the treatment fluid into the wellbore. In some embodiments, the biocide is selected from the group consisting of a quaternary ammonium compound, chlorine, a hypochlorite solution, sodium dichloros-triazinetrione, glutaraldehyde, a quaternary phosphonium compound, an isothiazolinone, oxazolidine, sodium bromide, chlorine dioxide, bronopol, triazine, chlorine dioxide, peracetic acid, 2,2-dibromo-3-nitrilopropionamide (DBNPA), acrolein, and any combination thereof. In some embodiments, the fluid is a recycled fluid. In some embodiments, the indicator reagent is selected from the group consisting of ferric ammonium citrate, ferrous sulfate, ammonium ferric sulfate, any derivative thereof, and any combination thereof. In some embodiments, at least one of the one or more microorganisms includes sulfate reducing bacteria (SRB). In some embodiments, the first sample of the fluid has less than 1% total dissolved solids by weight. In some embodiments, the first sample of the fluid has greater than 10% total dissolved solids by weight. In some embodiments, the method further includes determining a biocide for treating the fluid based, at least in part, on the first count of the microorganisms in the fluid. In some embodiments, the method further includes introducing the biocide into the fluid to produce a treatment fluid; and introducing the fluid into a wellbore penetrating at least a portion of a subterranean formation.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to those skilled in the art having the benefit of the teachings herein. While numerous changes may be made by those skilled in the art, such changes are encompassed within the spirit of the subject matter defined by the appended claims. Furthermore, no limitations are intended to the details of construction or design herein shown, other than as described in the claims below. It is therefore evident that the particular illustrative embodiments disclosed above may be altered or modified and all such variations are considered within the scope and spirit of the present disclosure. In particular, every range of values (e.g., "from about a to about b," or, equivalently, "from approximately a to b," or, equivalently, "from approximately a-b") disclosed herein is to be understood as referring to the power set (the set of all subsets) of the respective range of values. The terms in the claims have their plain, ordinary meaning unless otherwise explicitly and clearly defined by the patentee.

What is claimed is:

1. A method for assessing a fluid for use in preparation of a treatment fluid for servicing a wellbore penetrating a subterranean formation, the method comprising:
   providing a fluid comprising an aqueous base fluid and bacteria, wherein the bacteria comprises sulfate-reducing bacteria (SRB), nitrate-reducing bacteria, or acid producing bacteria (APB), or combinations thereof;
   introducing a first sample of the fluid to a first culture device comprising a first indicator reagent, wherein the first indicator reagent is configured to provide a detectable indication of presence of the bacteria or a byproduct thereof, wherein the first indicator reagent comprises a reagent for detecting hydrogen sulfide production by bacteria, a pH indicator, a redox indicator, a chromogenic enzyme substrate, a fluorogenic enzyme substrate, or a combination thereof, wherein over a period of about 48 hours or less the first indicator reagent indicates a first color change in the first sample of the fluid;
   determining, within the period of about 48 hours or less, a first count of the bacteria in the fluid based, at least in part, on a degree of color change and a rate of color change associated with the first color change;
   introducing a second sample of the fluid comprising a biocide to a second culture device comprising a second indicator reagent, wherein the second indicator reagent is configured to provide a detectable indication of presence of the bacteria or a byproduct thereof, wherein the second indicator reagent comprises a reagent for detecting hydrogen sulfide production by bacteria, a pH indicator, a redox indicator, a chromogenic enzyme substrate, a fluorogenic enzyme substrate, or a combination thereof, wherein over a period of about 48 hours or less the second indicator reagent indicates a second color change in the second sample of the fluid;
   determining, within the period of about 48 hours or less, a second count of the bacteria in the second sample of the fluid based, at least in part, on a degree of color change and a rate of color change associated with the second color change;
   selecting a treatment biocide based, at least in part, on the first count and the second count of the bacteria;
   contacting the fluid with the treatment biocide to produce a treatment fluid; and
   introducing the treatment fluid into a wellbore penetrating at least a portion of a subterranean formation.

2. The method of claim 1 wherein the first culture device is a thin-film culture device.

3. The method of claim 1 wherein the first indicator reagent, the second indicator reagent, or both the first indicator reagent and the second indicator reagent is selected from the group consisting of ferric ammonium citrate, ferrous sulfate, ammonium ferric sulfate, any derivative thereof, and any combination thereof.

4. The method of claim 1 wherein bacteria comprises SRB.

5. The method of claim 1 wherein the first sample of the fluid has less than 1% total dissolved solids by weight.

6. The method of claim 1 wherein the first sample of the fluid has greater than 10% total dissolved solids by weight.

7. A method for assessing a fluid for use in preparation of a treatment fluid for servicing a wellbore penetrating a subterranean formation, the method comprising:
   providing a fluid comprising an aqueous base fluid and bacteria, wherein the bacteria comprises sulfate-reducing bacteria (SRB), nitrate-reducing bacteria, or acid producing bacteria (APB), or combinations thereof;

introducing a first sample of the fluid comprising a biocide to a first culture device comprising an indicator reagent, wherein the indicator reagent is configured to provide a detectable indication of presence of the bacteria or a byproduct thereof, wherein the indicator reagent comprises a reagent for detecting hydrogen sulfide production by bacteria, a pH indicator, a redox indicator, a chromogenic enzyme substrate, a fluorogenic enzyme substrate, or a combination thereof, wherein over a period of about 48 hours or less the indicator reagent indicates a first color change in the first sample of the fluid;

determining, within the period of about 48 hours or less, a first count of the bacteria in the fluid based, at least in part, on a degree of color change and a rate of color change associated with the first color change;

selecting a treatment biocide based, at least in part, on the first count of the bacteria;

contacting the fluid with the treatment biocide to produce a treatment fluid; and introducing the treatment fluid into a wellbore penetrating at least a portion of a subterranean formation.

8. The method of claim 7 wherein the biocide is selected from the group consisting of a quaternary ammonium compound, chlorine, a hypochlorite solution, sodium dichloro-s-triazinetrione, glutaraldehyde, a quaternary phosphonium compound, an isothiazolinone, oxazolidine, sodium bromide, chlorine dioxide, bronopol, triazine, chlorine dioxide, peracetic acid, 2,2-dibromo-3-nitrilopropionamide (DBNPA), acrolein, and any combination thereof.

9. The method of claim 7 wherein the first culture device is a thin-film culture device.

10. The method of claim 7 wherein the indicator reagent is selected from the group consisting of ferric ammonium citrate, ferrous sulfate, ammonium ferric sulfate, any derivative thereof, and any combination thereof.

11. The method of claim 7 wherein bacteria comprises SRB.

12. The method of claim 7 wherein the first sample of the fluid has less than 1% total dissolved solids by weight.

13. The method of claim 7 wherein the first sample of the fluid has greater than 10% total dissolved solids by weight.

14. A method for assessing a fluid for use in preparation of a treatment fluid for servicing a wellbore penetrating a subterranean formation, the method comprising:

providing a fluid comprising an aqueous base fluid and bacteria, wherein the bacteria comprises sulfate-reducing bacteria (SRB), nitrate-reducing bacteria, or acid producing bacteria (APB), or combinations thereof;

introducing a first sample of the fluid comprising a first biocide to a first culture device comprising a first indicator reagent, wherein the first indicator reagent is configured to provide a detectable indication of presence of the bacteria or a byproduct thereof, wherein the first indicator reagent comprises a reagent for detecting hydrogen sulfide production by bacteria, a pH indicator, a redox indicator, a chromogenic enzyme substrate, a fluorogenic enzyme substrate, or a combination thereof, wherein over a period of about 48 hours or less the first indicator reagent indicates a first color change in the first sample of the fluid;

determining, within the period of about 48 hours or less, a first count of the bacteria in the first sample of the fluid based, at least in part, on a degree of color change and a rate of color change associated with the first color change;

introducing a second sample of the fluid comprising a second biocide to a second culture device comprising a second indicator reagent, wherein the second indicator reagent is configured to provide a detectable indication of presence of the bacteria or a byproduct thereof, wherein the second indicator reagent comprises a reagent for detecting hydrogen sulfide production by bacteria, a pH indicator, a redox indicator, a chromogenic enzyme substrate, a fluorogenic enzyme substrate, or a combination thereof, wherein over a period of about 48 hours or less the second indicator reagent indicates a second color change in the second sample of the fluid;

determining, within the period of about 48 hours or less, a second count of the bacteria in the second sample of the fluid based, at least in part, on a degree of color change and a rate of color change associated with the second color change;

selecting a treatment biocide from the first biocide and the second biocide, based, at least in part, on a comparison of the first count of the bacteria and the second count of the bacteria;

contacting the fluid with the treatment biocide to produce a treatment fluid; and introducing the treatment fluid into a wellbore penetrating at least a portion of a subterranean formation.

15. The method of claim 14, wherein the fluid is contacted with the treatment biocide for at least a period of about four hours before introducing the treatment fluid into the wellbore.

16. The method of claim 14, wherein the fluid is contacted with the treatment biocide for at least a period of about twenty-four hours before introducing the treatment fluid into the wellbore.

17. The method of claim 14 wherein the first biocide and the second biocide are independently selected from the group consisting of a quaternary ammonium compound, chlorine, a hypochlorite solution, sodium dichloro-s-triazinetrione, glutaraldehyde, a quaternary phosphonium compound, an isothiazolinone, oxazolidine, sodium bromide, chlorine dioxide, bronopol, triazine, chlorine dioxide, peracetic acid, 2,2-dibromo-3-nitrilopropionamide (DBNPA), acrolein, and any combination thereof.

18. The method of claim 1, wherein the detectable indication provided by the first indicator reagent, the second indicator reagent, or both the first indicator reagent and the second indicator reagent comprises a color change or fluorescence.

19. The method of claim 7, wherein the detectable indication provided by the indicator reagent comprises a color change or fluorescence.

20. The method of claim 14, wherein the detectable indication provided by the first indicator reagent, the second indicator reagent, or both the first indicator reagent and the second indicator reagent comprises a color change or fluorescence.

21. The method of claim 1 wherein the biocide is selected from the group consisting of a quaternary ammonium compound, chlorine, a hypochlorite solution, sodium dichloro-s-triazinetrione, glutaraldehyde, a quaternary phosphonium compound, an isothiazolinone, oxazolidine, sodium bromide, chlorine dioxide, bronopol, triazine, chlorine dioxide, peracetic acid, 2,2-dibromo-3-nitrilopropionamide (DBNPA), acrolein, and any combination thereof.

22. The method of claim 14 wherein the bacteria comprises SRB.

\* \* \* \* \*